United States Patent
Chen et al.

(10) Patent No.: US 9,612,361 B2
(45) Date of Patent: Apr. 4, 2017

(54) OPTICAL COMPUTING DEVICE DIAGNOSTICS AND TREATMENT

(71) Applicant: Halliburton Energy Services, Inc., Houston, TX (US)

(72) Inventors: Dingding Chen, Tomball, TX (US); David L. Perkins, The Woodlands, TX (US); William Soltmann, The Woodlands, TX (US); Darren Gascooke, Houston, TX (US); Jing Shen, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/780,780

(22) PCT Filed: Dec. 12, 2014

(86) PCT No.: PCT/US2014/069935
§ 371 (c)(1),
(2) Date: Sep. 28, 2015

(87) PCT Pub. No.: WO2016/093853
PCT Pub. Date: Jun. 16, 2016

(65) Prior Publication Data
US 2016/0327684 A1    Nov. 10, 2016

(51) Int. Cl.
*G01N 21/00* (2006.01)
*G01V 13/00* (2006.01)
(Continued)

(52) U.S. Cl.
CPC .............. *G01V 13/00* (2013.01); *E21B 47/06* (2013.01); *E21B 47/065* (2013.01);
(Continued)

(58) Field of Classification Search
CPC ................. H01J 37/32935; G01J 3/02; G01N 2015/1037; G01N 21/64; G01N 21/68
See application file for complete search history.

(56) References Cited

U.S. PATENT DOCUMENTS

| 2004/0161370 A1* | 8/2004 | Sunshine | G01N 33/0006 422/83 |
| 2009/0194330 A1* | 8/2009 | Gray | E21B 21/00 175/24 |

(Continued)

FOREIGN PATENT DOCUMENTS

EP    2199999 A1    6/2010

OTHER PUBLICATIONS

International Search Report and Written Opinion for PCT/US2014/069935 dated Aug. 25, 2015.

*Primary Examiner* — Tarifur Chowdhury
*Assistant Examiner* — Md M Rahman
(74) *Attorney, Agent, or Firm* — McDermott Will & Emery LLP; Alan Bryson (57) ABSTRACT

An example method includes performing validation testing on a tool using a plurality of reference fluids, the tool having a calibrated optical sensor installed therein that includes one or more optical elements. One or more tool sensor responses from the calibrated optical sensor may be obtained and pre-processed, and the one or more tool sensor responses may be compared with calibrated optical sensor responses derived from the calibrated optical sensor during calibration and thereby detecting one or more optical sensor anomalies. The one or more optical sensor anomalies may be evaluated through performance analysis with one or more candidate models, and an alternative candidate model may be selected to mitigate the one or more optical sensor anomalies. One or more remedial options may be pursued when the alternative
(Continued)

candidate model fails to mitigate the one or more optical sensor anomalies.

23 Claims, 8 Drawing Sheets

(51) Int. Cl.
*E21B 47/10* (2012.01)
*G01V 8/02* (2006.01)
*G01N 21/27* (2006.01)
*E21B 47/06* (2012.01)
*E21B 49/08* (2006.01)

(52) U.S. Cl.
CPC .......... *E21B 47/102* (2013.01); *E21B 49/082* (2013.01); *G01N 21/274* (2013.01); *G01V 8/02* (2013.01)

(56) References Cited

U.S. PATENT DOCUMENTS

| | | |
|---|---|---|
| 2010/0082258 A1 | 4/2010 | Wang |
| 2011/0270797 A1* | 11/2011 | Adams .................... G06N 7/00 706/59 |
| 2012/0290208 A1 | 11/2012 | Jiang et al. |
| 2012/0323494 A1 | 12/2012 | Lovell et al. |
| 2013/0311099 A1 | 11/2013 | Eyuboglu et al. |
| 2014/0188404 A1* | 7/2014 | Von Herzen ........... F01M 11/10 702/31 |

* cited by examiner

|      | GOL33 | GOL13 | H2O   | TOL   | PEN   | DOD   | N2    |
|------|-------|-------|-------|-------|-------|-------|-------|
| Ch01 | 7.39  | 0.18  | 1.35  | 8.88  | 6.35  | 0.35  | 0.50  |
| Ch02 | 7.41  | 9.03  | 44.45 | 16.60 | 10.51 | 7.19  | 15.91 |
| Ch03 | 16.86 | 18.95 | 57.71 | 30.72 | 22.37 | 16.94 | 28.71 |
| Ch04 | 31.59 | 31.38 | 0.87  | 39.04 | 46.17 | 31.81 | 28.59 |
| Ch05 | 0.26  | 0.28  | 9.88  | 3.22  | 12.73 | 1.11  | 0.08  |
| Ch06 | 60.18 | 56.01 | 34.01 | 54.35 | 43.12 | 59.59 | 1.34  |
| Ch07 | 12.58 | 10.76 | 0.54  | 11.68 | 6.68  | 12.75 | 1.74  |
| Ch08 | 10.05 | 15.99 | 0.64  | 26.12 | 0.93  | 27.23 | 1.52  |
| Ch09 | 0.15  | 0.83  | 1.25  | 13.64 | 1.57  | 0.77  | 30.78 |
| Ch10 | 12.07 | 10.52 | 1.32  | 18.53 | 0.76  | 17.27 | 34.91 |
| Ch11 | 5.32  | 1.57  | 4.09  | 6.39  | 3.18  | 3.67  | 10.02 |
| Ch12 | 1.60  | 1.56  | 1.79  | 2.70  | 7.44  | 0.06  | 0.56  |
| Ch13 | 6.37  | 2.27  | 0.92  | 9.24  | 9.02  | 2.06  | 3.30  |
| Ch14 | 2.89  | 1.26  | 19.91 | 4.36  | 4.16  | 1.08  | 2.00  |
| Ch15 | 1.70  | 0.37  | 0.85  | 8.41  | 2.95  | 3.46  | 0.69  |
| Ch16 | 0.73  | 0.24  | 22.47 | 0.22  | 9.07  | 0.65  | 0.45  |

FIG. 5A

|      | GOL33 | GOL13 | H2O   | TOL   | PEN   | DOD   | N2    |
|------|-------|-------|-------|-------|-------|-------|-------|
| Ch17 | 1.43  | 0.02  | 0.41  | 0.33  | 6.33  | 0.04  | 0.86  |
| Ch18 | 1.27  | 0.68  | 0.55  | 2.17  | 7.20  | 0.95  | 1.17  |
| Ch19 | 0.83  | 0.30  | 0.39  | 1.99  | 6.92  | 0.79  | 0.28  |
| Ch20 | 6.25  | 7.35  | 40.71 | 0.05  | 8.62  | 6.24  | 1.14  |
| Ch21 | 3.51  | 2.42  | 3.02  | 0.36  | 22.58 | 0.85  | 2.83  |
| Ch22 | 0.59  | 0.79  | 30.63 | 2.05  | 18.59 | 0.05  | 1.59  |
| Ch23 | 0.64  | 0.32  | 4.68  | 8.22  | 0.54  | 0.34  | 0.48  |
| Ch24 | 9.85  | 15.81 | 1.18  | 5.80  | 1.46  | 0.21  | 1.23  |
| Ch25 | 1.00  | 1.44  | 1.85  | 12.74 | 2.42  | 0.11  | 1.71  |
| Ch26 | 6.21  | 8.58  | 10.14 | 6.30  | 10.61 | 8.04  | 1.83  |
| Ch27 | 2.44  | 4.92  | 5.19  | 11.32 | 6.05  | 7.72  | 58.85 |
| Ch28 | 1.10  | 1.05  | 0.05  | 8.59  | 1.91  | 3.54  | 63.51 |
| Ch29 | 2.14  | 2.29  | 2.15  | 6.18  | 13.50 | 4.10  | 1.84  |
| Ch30 | 2.54  | 3.19  | 5.82  | 8.99  | 15.44 | 6.57  | 2.92  |
| Ch31 | 5.50  | 2.92  | 5.60  | 5.50  | 8.45  | 2.89  | 5.68  |
| Ch32 | 0.70  | 1.42  | 2.46  | 3.72  | 3.13  | 3.08  | 1.79  |

OPTICAL COMPUTING DEVICE DIAGNOSTICS AND TREATMENT

This application is a National Stage entry of and claims priority to International Application No. PCT/US2014/069935, filed on Dec. 12, 2014.

BACKGROUND

Optical computing devices, also commonly referred to as "opticoanalytical devices," can be used to analyze and monitor a substance in real time. Such optical computing devices will often employ an optical element or optical processing element that optically interacts with the substance or a sample thereof to determine quantitative and/or qualitative values of one or more physical or chemical properties of the substance. The optical element may be, for example, an integrated computational element (ICE) core, also known as a multivariate optical element (MOE), which is essentially an optical interference based device that can be designed to operate over a continuum of wavelengths in the electromagnetic spectrum from the UV to mid-infrared (MIR) ranges, or any sub-set of that region. Electromagnetic radiation that optically interacts with a substance is changed and processed by the ICE core so as to be readable by a detector, such that an output of the detector can be correlated to the physical or chemical property of the substance being analyzed.

An ICE core typically includes a plurality of optical layers consisting of various materials whose index of refraction and size (e.g., thickness) may vary between each layer. An ICE core design refers to the number and thickness of the respective layers of the ICE core. The layers may be strategically deposited and sized so as to selectively pass predetermined fractions of electromagnetic radiation at different wavelengths configured to substantially mimic a regression vector corresponding to a particular physical or chemical property of interest of a substance. Accordingly, an ICE core design will exhibit a transmission function that is weighted with respect to wavelength. As a result, the output light intensity from the ICE core conveyed to a detector may be related to the physical or chemical property of interest for the substance.

After manufacture, and before being placed in downhole use, each optical computing device must be carefully calibrated against known reference fluids for temperature and pressure ranges expected to be encountered in the field. The calibrated optical computing devices are then installed as part of a downhole tool and re-tested to validate the optical responses from the optical element. In some cases, anomalous optical responses may occur upon field-testing the optical computing device. An anomalous optical response essentially consists of an optical response that is either too high or too low as compared to the calibration data. Optical response anomalies can be caused by, for example, damage to an optical element (e.g., a light focusing or collimating element), the changes in optical fastening materials under the stress of high temperatures and pressures. Optical response anomalies can arise after replacement of parts during servicing of the tool resulting in inconsistencies between optical system components and signal processing between the manufacturing calibration and tool implementation. Other sources of optical response anomalies can result from assembly and/or disassembly variations of the optical computing device in the downhole tool.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure relates to optical computing devices and, more particularly, to systems and methods for calibrating optical computing devices or optical sensors that use optical elements.

The embodiments described herein provide new methods of detecting optical sensor anomalies based on optical sensor responses and the performance measures obtained from tool validation testing and field testing. The presently described methods improve real-time software predictions using the validated inputs of optical channels associated with the optical sensor. More particularly, a variable-input-model based performance evaluation method is provided for optical sensor diagnostics, which may be applicable to pressure-volume-temperature (PVT) characterization, optical sensor manufacturing calibration, tool validation testing, and field data post-processing. As a result, the need for complicated uncertainty analysis associated with using nonlinear modeling framework may be substantially eliminated. The methods described herein may prove advantageous in allowing an operator to detect and address optical sensor anomalies and enable decisions about recalibration or optical element replacement, when needed.

The terms "optical computing device" and "optical sensor" are used herein interchangeably and refer generally to a sensor configured to receive an input of electromagnetic radiation that has interacted with a substance and produce an output of electromagnetic radiation from an optical element arranged within or otherwise forming part of the optical computing device. The processing element may be, for example, an integrated computational element (ICE core), also known as a multivariate optical element (MOE). Prior to field use, the optical computing device, and each optical element employed therein, must be calibrated such that each is able to operate effectively upon being exposed to downhole conditions. If they are not properly calibrated, the resulting transmission functions derived from each optical element may provide well operators with inaccurate measurements upon deployment.

Figure 1:
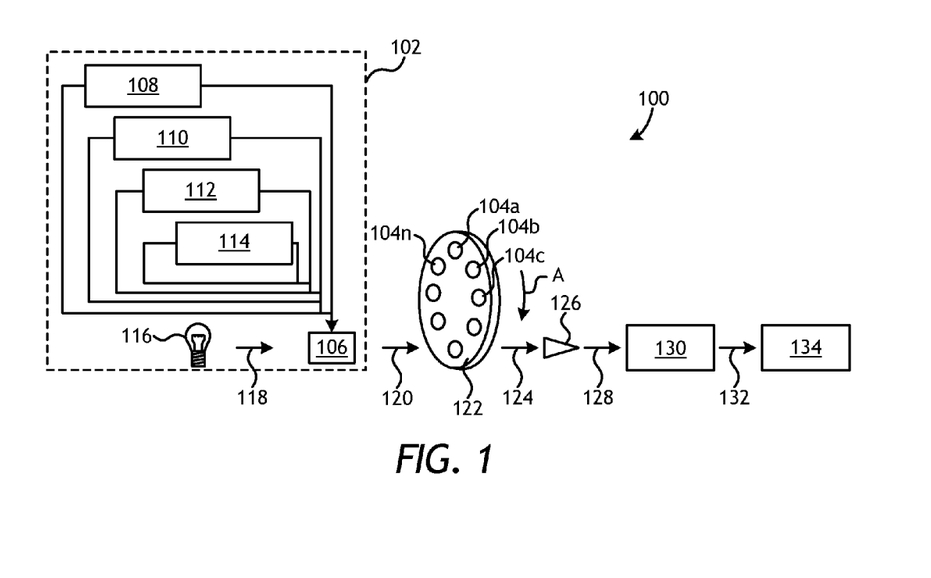
FIG. 1 illustrates a calibration system that may be used to calibrate one or more optical elements.

FIG. 1 illustrates an exemplary manufacturing calibration system 100 that may be used to calibrate one or more optical elements used in an optical sensor. As illustrated, the system 100 may include a measurement system 102 in optical communication with one or more optical elements 104 (shown as 104a, 104b, 104c . . . 104n) that are to be calibrated. Each optical element 104a-n may be either an optical bandpass filter or a multivariate optical element/integrated computational element (e.g., an ICE core). The measurement system 102 may circulate one or more reference fluids with different chemical compositions and properties (i.e., methane concentration, saturates concentration, gas/oil ratio or "GOR", etc.) through an optic cell 106 over widely varying calibration conditions of temperature, pressure, and density, such that optical transmission and/or reflection measurements of each reference fluid in conjunction with each optical element 104a-n may be made at such conditions.

The measurement system 102 may comprise an optical pressure-volume-temperature (PVT) instrument, and the reference fluids circulated in the measurement system 102 may comprise representative fluids commonly encountered in downhole applications. The system 100 may collect output signals from each optical element 104a-n for each specified reference fluid at varying calibration conditions. In some cases, the reference fluids may comprise seven representative fluids that are easy to operate for manufacturing calibration, namely, dodecane, nitrogen, water, toluene, 1-5 pentanediol, and two liquid crude oils or fluids with no gas concentration (e.g., dead oil). The crude reservoir oils used as reference fluids may be, for example, global oil library 13 (or "GOL13"), and global oil library 33 (or "GOL33"). In other cases, the reference fluids may include samples of live oils mixed with dead oil and hydrocarbon gas, such as methane for example, and the samples of hydrocarbon gases and/or $CO_2$. Manufacturing calibration of the optical sensor may serve the need of detector output re-scaling or instrument standardization.

The measurement system 102 may vary each reference fluid over several set points spanning varying calibration conditions. To accomplish this, as illustrated, the measurement system 102 may include a liquid charging system 108, a gas charging system 110, a temperature control system 112, and a pressure control system 114. The liquid charging system 108 injects fluids into the fluid circuit to introduce fluid varying perturbations such that calibrating the optical elements 104a-n will incorporate all the expected compounds found in the particular reference fluid. The gas charging system 110 may inject known gases (e.g., $N_2$, $CO_2$, $H_2S$, methane, propane, ethane, butane, combinations thereof, and the like) into the circulating reference fluids. The temperature control system 112 may vary the temperature of the reference fluid to simulate several temperature set points that the optical elements 104a-n may encounter downhole. Lastly, the pressure control system 114 may vary the pressure of the reference fluid to simulate several pressure set points that the optical elements 104a-n may encounter downhole.

The optic cell 106 is fluidly coupled to each system 108, 110, 112, and 114 to allow the reference fluids to flow therethrough and recirculate back to each of the systems 108, 110, 112, and 114 in a continuous, closed-loop fluid circuit. While circulating through the optic cell 106, a light source 116 emits electromagnetic radiation 118 that passes through the optic cell 106 and the reference fluid flowing therethrough. As the electromagnetic radiation 118 passes through the optic cell 106 it optically interacts with the reference fluid and generates sample interacted light 120, which includes spectral data for the particular reference fluid circulating through the measurement system 102 at the given calibration conditions or set points. The sample interacted light 120 may be directed toward the optical elements 104a-n which, as illustrated, may be arranged or otherwise disposed on a sensor wheel 122 configured to rotate in the direction A. While shown as arranged in a single ring on the sensor wheel 122, the optical elements 104a-n may alternatively be arranged in two or more rings on the filter wheel 122.

During calibration, the sensor wheel 122 may be rotated at a predetermined frequency such that each optical element 104a-n may optically interact with the sample interacted light 120 for a brief period and sequentially produce optically interacted light 124 that is conveyed to a detector 126. The detector 126 may be generally characterized as an optical transducer and may comprise, but is not limited to, a thermal detector (e.g., a thermopile), a photoacoustic detector, a semiconductor detector, a piezo-electric detector, a charge coupled device (CCD) detector, a video or array detector, a split detector, a photon detector (e.g., a photomultiplier tube), photodiodes, and any combination thereof. Upon receiving individually-detected beams of optically interacted light 124 from each optical element 104a-n, the detector 126 may generate or otherwise convey corresponding response signals 128 to a data acquisition system 130. The data acquisition system 130 may time multiplex each response signal 128 received from the detector 126 corresponding to each optical element 104a-n. A corresponding set of resulting output signals 132 is subsequently generated and conveyed to a data analysis system 134 for processing and providing input parameters for various fluid predictive models with use of outputs from each optical element 104a-n as a candidate variable.

Once the sensor wheel 122 is calibrated, one or more calibrated sensor wheels 122 may then be installed on an optical tool with other system components and otherwise placed in an optical computing device for assembly validation testing. To validate an optical response of the optical tool as installed in the optical computing device, the optical computing device may be placed in an oven that regulates the ambient temperature and pressure. The reference fluids used to calibrate the sensor wheel 122 may then be selectively circulated through the optical tool at similar set points used to calibrate the optical elements 104a-n. More particularly, the reference fluids may be circulated through the optical tool at various set point downhole conditions (i.e., elevated pressures and temperatures) to obtain measured optical responses.

While manufacturing calibration of the sensor wheel 104a-n using reference fluids is performed in real optical sensor or tool parameter space, fluid spectroscopic analysis and fluid predictive model calibration using big data in a standard oil library is performed in synthetic optical sensor parameter space (also called Optical-PVT data space). Synthetic sensor response of each element is calculated as a dot product of full-wavelength-range of fluid spectrometry and sensor element spectrum excited by a light source, which might nonlinearly or linearly vary in scale compared to the actual sensor response due to the difference between the mathematic approximation used in calculating synthetic sensor response and the real system implementation. To compensate for the difference above, the measurement data from the optical tool can be transformed from the tool parameter space to the synthetic sensor parameter space first through a data mapping or standardization algorithm before applying fluid predictive models. Also, fluid predictive models can be calibrated with different synthetic optical inputs and saved in an optical fluid model base to provide sufficiency and adaptation in dealing with uncertainty of data transformation and improving formation fluid compositional analysis and field data interpretation.

In current practice, an optical fluid model base is sensor dependent, including data transformation (i.e., standardization) models and property predictive models. To provide adequate flexibility for optical data processing and interpretation, an optical fluid model base includes the following candidate constituents: transformation models calibrated on selected reference fluids through reverse transformation, transformation models calibrated on selected reference fluids through forward transformation, and predictive models calibrated on both Optical-PVT database and sensor wheel 122 data spaces.

Figure 2:
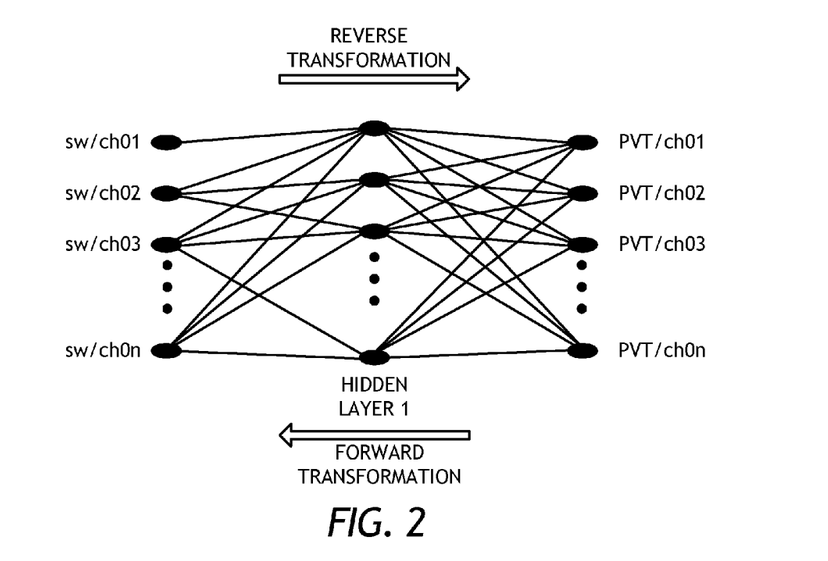
FIG. 2 illustrates a general transformation model framework.

Transformation model development using the selected reference fluids requires matched calibration data pairs of optical sensor responses simulated in the Optical-PVT data space and measured in the sensor wheel 122 data space. In Optical-PVT data space, simulated sensor responses on reference fluids are available at the ideal temperature and pressure setting points. Measured optical responses of the sensor wheel 122 may endure slight temperature and pressure variation during manufacturing calibration. The matched transformation data pairs are obtained through two-dimensional interpolation by using actual temperatures and pressures as inputs to generate simulated sensor responses at the corresponding measurement conditions. Depending on the data space in which the fluid property predictive models are calibrated, data transformation models convert measured or simulated optical sensor output from one data space to another data space. FIG. 2 illustrates one such transformation.

More particularly, FIG. 2 illustrates an embodiment of a general transformation model framework with a multi-input, multi-output neural network that may be applied by the data analysis system 134 of FIG. 1 to optical responses. The model that converts the actual optical sensor response channels (SW/Ch01-Ch0*n*) to the simulated Optical-PVT sensor response channels (PVT/Ch01-Ch0*n*) can be referred to as the reverse transformation model. The model that converts the optical sensor response to the simulated Optical-PVT sensor response can be referred to as the forward transformation model. Although the illustrated general transformation model framework in FIG. 2 is configured with multi-input/multi-output non-linear neural networks, there is no limitation in using other non-linear and linear transformation algorithms with single-input/single-output and multi-input/single-output configurations.

Figure 3:
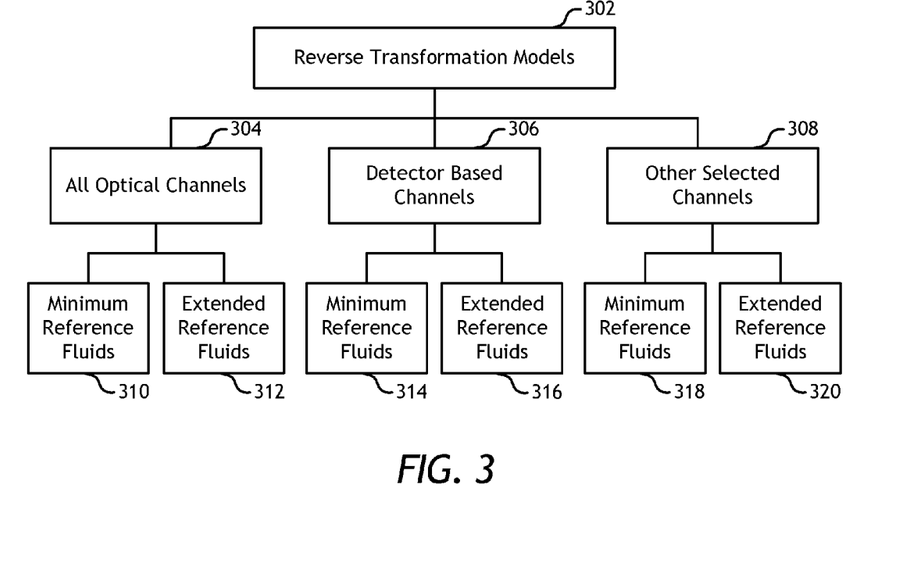
FIG. 3 depicts a hierarchical structure for reverse transformation models.

FIG. 3 illustrates an embodiment of a hierarchical structure for reverse transformation models 302. The variations of transformation models 302 may include converting optical channels 304 for each optical sensor in a single model, converting the disjoined optical channels in several detector-based models 306, or converting only selected channels 308 of interest each time in different individual models. Compared to a single model implementation, multi-model options can improve the reliability of data construction in the output (i.e., transformed) parameter domain if one or more of the optical channels, as a transformation input, experience a problem. The reference fluid blocks 310-320, at the bottom of the hierarchical structure and coupled to the various channels 304-308, represent the transformation models that can be built based on different reference fluids (e.g., minimum number of reference fluids 310, 314, 318 and extended reference fluids 312, 316, 320). The minimum number of reference fluids may refer to the seven representative fluids discussed above. These reference fluids are safe to use and easy to clean for testing purposes, and their optical sensor responses generally have a good coverage in data range as a representation of diverse fluids in an existing Optical-PVT database. Extended reference fluids often include one or more fluids such as live oil and/or gas to make the transformation model covering a wider range and more robust.

Reverse transformation models are designed to convert tool measurements into the Optical-PVT data space prior to applying predictive models calibrated on that data space. Forward transformation models can be used to convert a whole set of simulated optical sensor responses of an Optical-PVT database to the optical sensor/tool domain prior to developing predictive models on that domain. As seen in FIG. 2, a forward transformation model can be created by switching the input and the output of a neural network model. In other words, using an Optical-PVT synthetic-channel response as an input, and a measured sensor wheel channel response as an output. The neural network can then be retrained to calibrate forward transformation algorithms.

As will be appreciated, a hierarchical structure for the reverse transformation models 302, as illustrated in FIG. 3, can also be applied to forward transformation models. After the forward transformation model is developed, it can be used to convert the synthetic sensor responses of the global samples in the whole Optical-PVT database into the tool data space. Then the fluid property predictive models can be calibrated in tool data space, and the further transformation is not needed in field data processing because measured optical responses from the tool can be used as model inputs directly for fluid compositional analysis. Compared to the reverse transformation, which applies on-line tool data conversion each time before making a fluid prediction, forward transformation usually only applies one time off-line to convert Optical-PVT sensor responses for fluid prediction model development.

By applying a transformation model to the optical responses derived from the optical sensor, the optical sensor may be considered calibrated for use and ready for validation testing in any number of downhole tools or "tools." During tool validation testing, one or more calibrated optical sensors may be installed in a tool that is to be introduced downhole to obtain wellbore measurements using the calibrated optical sensors. In some embodiments, as described below, the tool may form part of a bottom hole assembly used in a drilling operation. In such embodiments, the tool may comprise any of a number of different types of tools including MWD (measurement-while-drilling) tools, LWD (logging-while-drilling) tools, and others. In other embodiments, however, the tool may be used in a wireline operation and otherwise form part of a wireline logging tool, such as a probe or sonde, to be lowered by wireline or logging cable into a borehole to obtain measurements.

Once the calibrated optical sensor(s) is installed in a tool, various reference fluids may be run through the tool at the same set points (i.e., elevated pressures and temperatures) used to calibrate the optical sensor(s). In some cases, the tool validation testing may be undertaken at a laboratory facility. In such cases, the same reference fluids used to calibrate the optical sensor may be used. In other cases, however, or in addition to laboratory testing, tool validation testing may be undertaken on-site, such as at a drill rig or wellhead installation where the tool is to be used in a wellbore operation. In such cases, a limited number of reference fluids may be used, such as water and nitrogen. Optical responses derived from the tool during validation testing may be normalized by using a transformation model (i.e., reverse, forward, etc.) that corrects the output of the tool validation process. The optical responses may then be compared against the optical responses of the calibrated optical sensor.

In some cases, optical sensor anomalies may be detected between the responses obtained while calibrating the optical sensor and the responses obtained during tool validation testing. The typical practice for sensor (not limited to optical sensors) anomaly detection is to set thresholds on output signals based on statistical analysis. For single output sensors or sensors with a small number of output channels, applying criterion is straightforward if the sensor output is a direct measurement of the target analyte or a predictor of the target through linear transformation. The impact of signal anomaly on model prediction can be evaluated via error distribution/transformation analysis. For multi-output sensors, such as the sensor wheel 122 of FIG. 1 and the associated optical sensors described herein, the drift in signal intensity can be observed but the tolerance is hard to determine. This is because the impact of a particular channel response on calibration models varies depending on the significance of that input to the target analyte. This is especially true when non-linear predictive models such as multi-layer neural networks with multi-channel inputs are used.

Figure 4A:
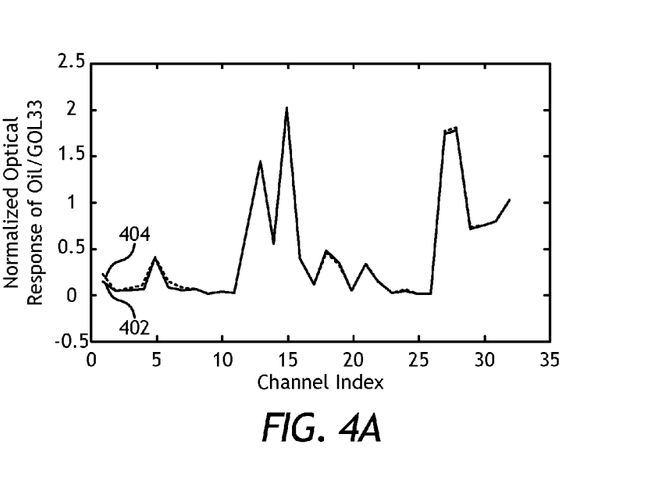
FIGS. 4A-4D are plots comparing normalized optical signal responses between sensor wheel calibration data and tool validation data.
Figure 4B:
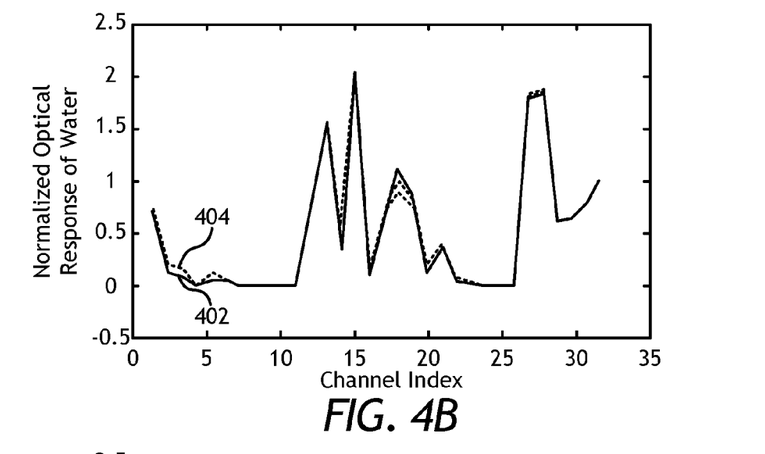
Figure 4C:
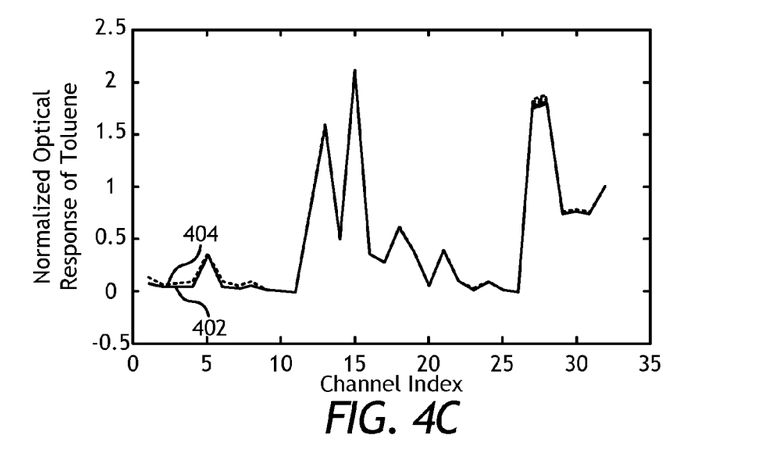
Figure 4D:
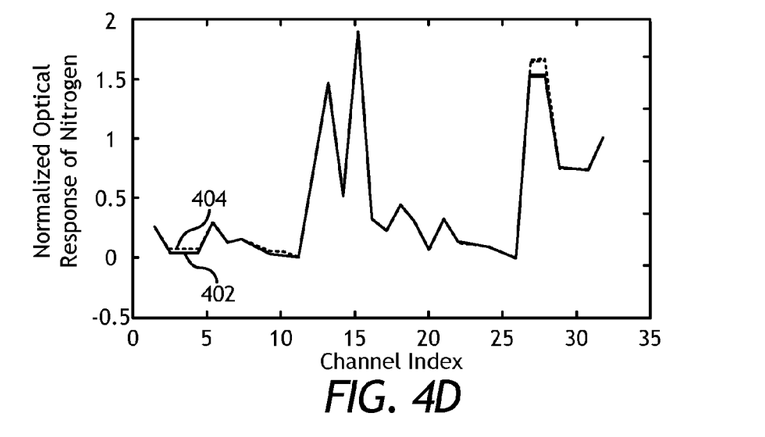

FIGS. 4A-4D are plots that compare normalized optical signal responses between the optical sensor calibration data and tool validation data after the tool has been assembled with the optical sensor. As illustrated, FIG. 4A shows a comparison in view of a reservoir fluid (e.g., GOL33) as a reference fluid, FIG. 4B shows a comparison in view of water as a reference fluid, FIG. 4C shows a comparison in view of toluene as a reference fluid, and FIG. 4C shows a comparison in view of nitrogen as a reference fluid. Each plot represents optical responses from thirty-two channels, which correspond to thirty-two optical elements of a sensor wheel (e.g., the sensor wheel 122 of FIG. 1). The first curve 402 in each plot represents the optical signal response from the tool during validation testing, and the second curve 404 in each plot represents the optical signal response from the calibrated optical sensor. Differences between the first and second curves 402, 404 indicate potential optical sensor anomalies.

Figure 5A:
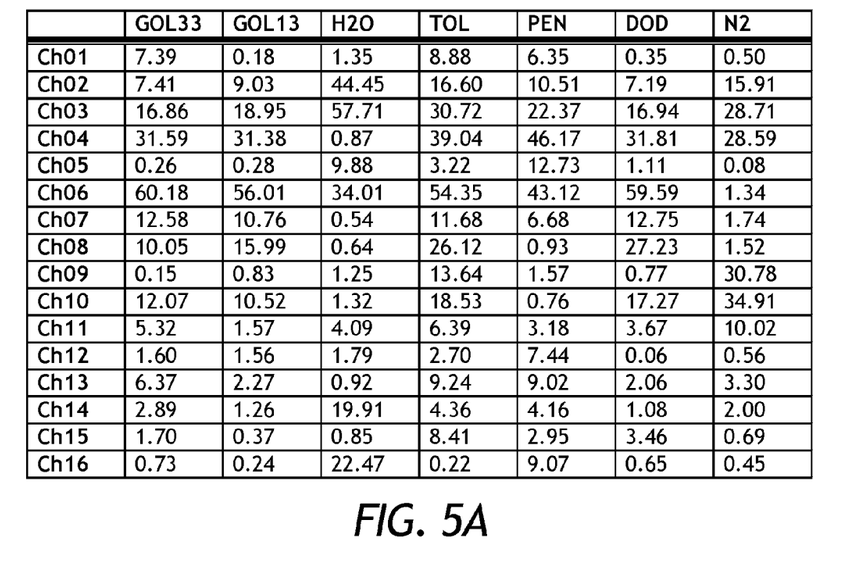
FIGS. 5A and 5B are data tables including additional testing reference fluids in addition to those shown in the plots of FIGS. 4A-4D.
Figure 5B:
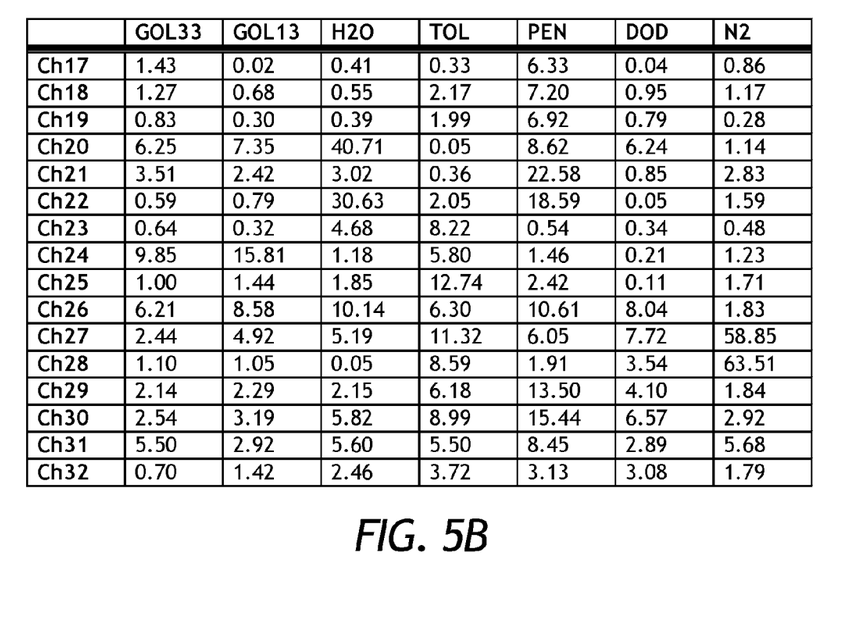

With continued reference to FIGS. 4A-4D, FIGS. 5A and 5B are data tables that provide calculations on the relative difference in signal intensity on each channel in view of the seven reference fluids, including those shown in the plots of FIGS. 4A-4D. More particularly, the tables in FIGS. 5A and 5B show testing data from CH01-Ch32 for oil/GOL13, oil/GOL33, water (H$_2$O), toluene (TOL), pentanediol (PEN), dodecane (DOD), and nitrogen (N$_2$). It can be observed that relative differences of normalized detector outputs on some channels might be significant, especially if the dynamic ranges of data on those channels are small. However, recalibration of the optical element or replacing the optical element in the optical sensor may not be necessary or recommended since optical sensor are often configured with redundant optical elements, and, as discussed above, the predictive models may be calibrated with variable optical sensor responses to maximize the likelihood of predictability of fluid properties in post-processing.

Figure 6:
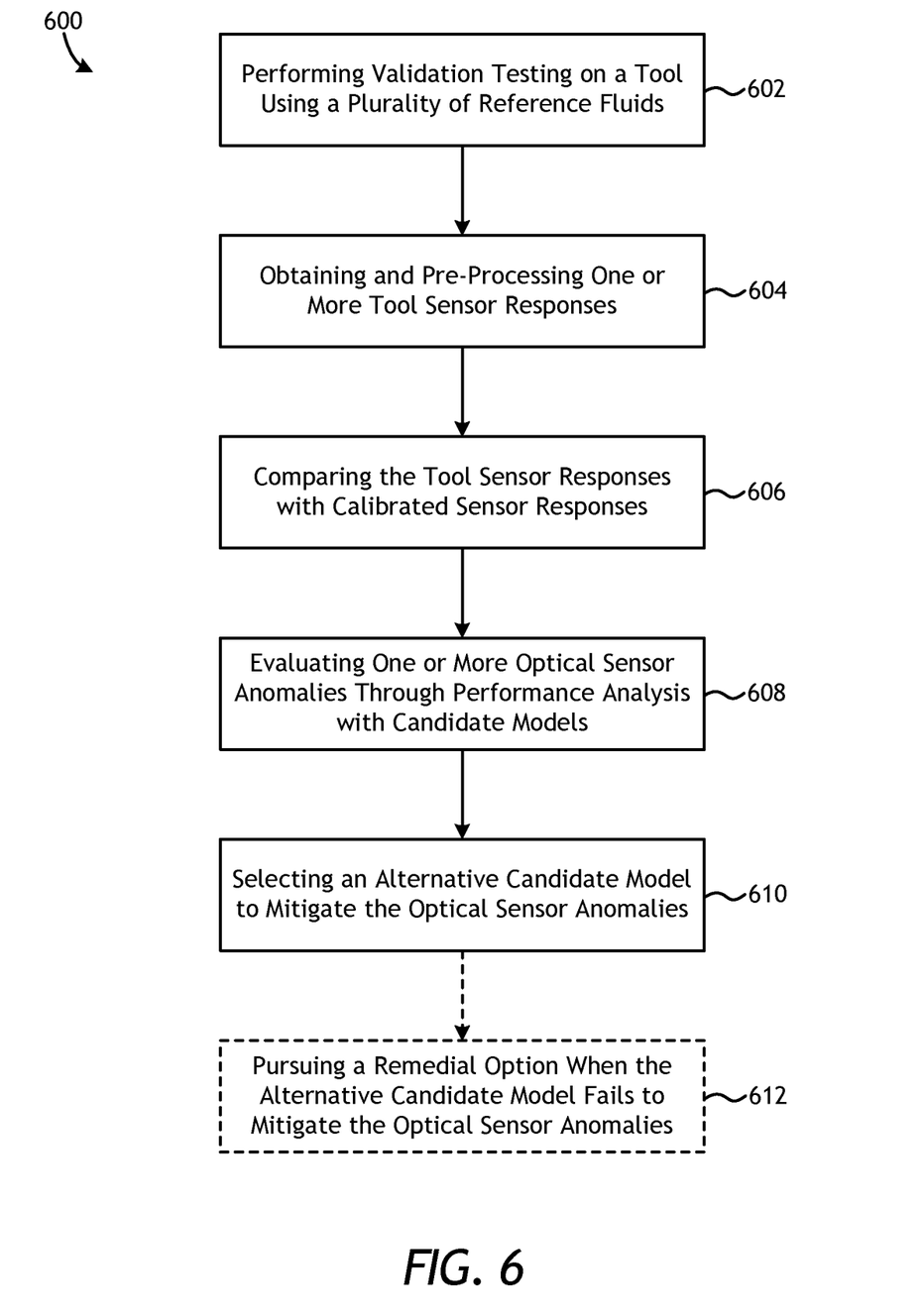
FIG. 6 is a schematic flowchart of a method for optical sensor diagnostics through model-based tool validation testing.
Figure 7A:
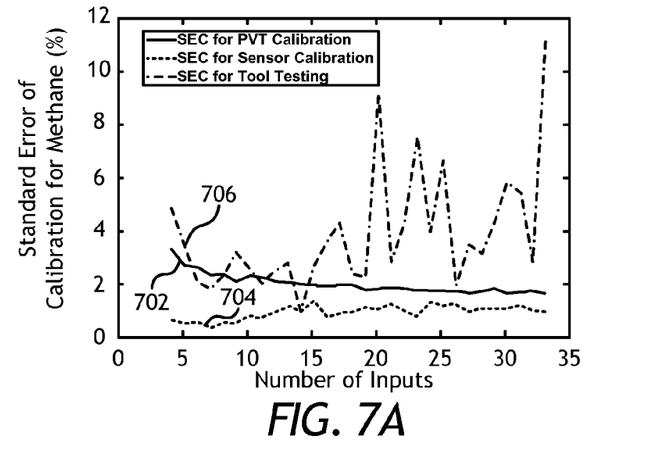
FIGS. 7A-7D are plots that show relative prediction variations of candidate models with different numbers of channel inputs from the same optical sensor.
Figure 7B:
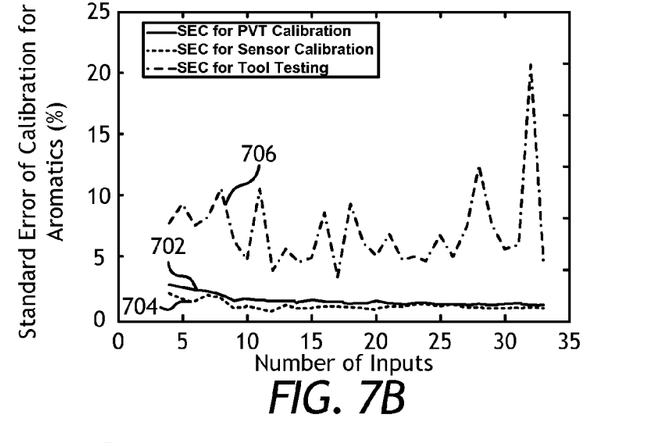
Figure 7C:
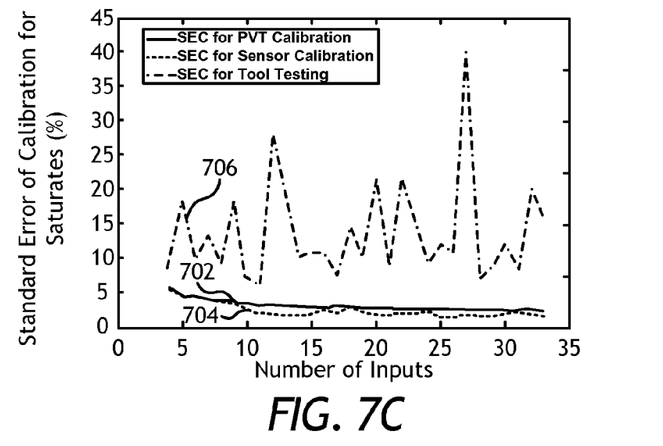
Figure 7D:
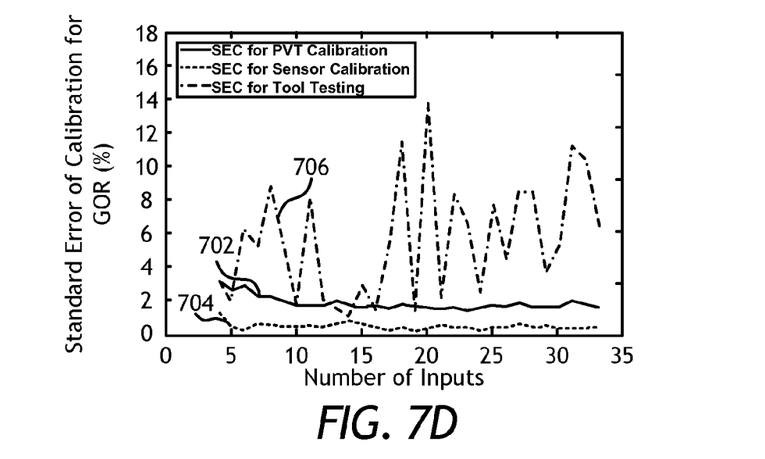

According to the present disclosure, methods are described herein that help detect optical sensor anomalies that deviate from the optical responses derived from the calibrated optical sensor during optical sensor calibration and evaluate the impact from the performance measurements during tool validation testing. Referring to FIG. 6, depicted is a schematic flowchart of a method 600 for optical sensor diagnostics through model-based tool validation testing, according to one or more embodiments. According to the method 600, validation testing may be undertaken on a tool using a plurality of reference fluids, as at 602. The validation test for the tool may be similar to the process described above with reference to tool validation testing. More particularly, after an optical sensor has been installed within the tool, various reference fluids may be circulated through the tool at one or more calibration set points. The optical sensor may include one or more optical elements and the calibration set points may be similar to the calibration set points used previously to calibrate the optical sensor and the one or more associated optical elements. Accordingly, the calibration set points may comprise specific temperature and pressure set points to test the tool.

As a result of the tool validation testing, tool sensor responses from the optical sensors installed in the tool may be obtained and pre-processed, as at 604. Obtaining and pre-processing the optical sensor responses may include directing light to interact with the reference fluid to produce interacted light, transmitting the interacted light toward the one or more optical elements, and generating detector responses over the one or more optical elements as the tool sensor responses. The measured tool sensor responses may then be baseline corrected and normalized, and the normalized tool sensor responses may be converted from a downhole tool data space to a calibration data space.

More particularly, data pre-processing of the optical sensor responses may be performed by subtracting the signal of a baseline channel from each optical channel. The baseline corrected detector response on each optical channel may then be divided by the light intensity of a neutral density channel to get the normalized signal response. The normalized signal response for the tool is represented by the first curve 402 in FIGS. 4A-4D for four reference fluids. As indicated above, the tool validation data in each plot of FIGS. 4A-4D is plotted against the measurements from the optical sensor during manufacturing calibration and before the tool is assembled. Both tool validation and prior optical sensor calibration data are collected at the same multiple temperature and pressure set points for comparison.

The method may further include comparing the one or more tool sensor responses from the tool with calibrated optical sensor responses derived from the optical sensor during calibration, as at 606. As mentioned above, the data tables of FIGS. 5A and 5B provide the calculated relative differences in normalized signal responses between optical sensor calibration and tool validation for an exemplary optical sensor. The calculation of relative difference may be based on the mean value of normalized measurements averaged over multiple set points for each reference fluid, and divided by the full range of signal intensity of entire calibration fluids for each optical channel. In the data table of FIG. 5A, for example, it can be observed that channels Ch03, Ch04, and Ch06 each exhibit larger percent difference in calibration and tool validation data as compared to the other channels. Their impact on future tool applications, however, may be difficult to determine before the predicted fluid properties with associated models using the tool validation data inputs are evaluated.

The impact of the differences between the tool optical sensor responses and the calibrated optical sensor outputs may then be evaluated through performance analysis with candidate models, as at 608. Performance analysis with tool validation data may be associated with the use of instrument standardization models and fluid characterization models, as generally described above. The instrument standardization algorithms or reverse transformation algorithms may be required when the fluid property predictive models are calibrated with an optical-PVT type database rather than in actual optical sensor or tool parameter space. In performance analysis, the normalized optical responses from the tool may be used as inputs of a non-linear or linear standardization model, which is sensor dependent, to convert actual optical sensor responses on each optical channel to the standard synthetic sensor response compatible with the calibration database of fluid property predictive models. The transformed optical responses on the validation reference fluids may then be used as candidate inputs to various calibration models in a model base to predict multiple fluid properties.

The calibration model base may be built in such a way that each fluid property can be predicted from a range (small to large) number of inputs (i.e., optical channels). The model base may also include models calibrated on redundant optical elements and non-identical optical elements, respectively. When an abnormal signal response is detected on a specific optical channel, it may affect the related model predictions from that optical channel only. The other candidate models may be less affected if the calibration inputs exclude the problematic optical channel. For example, a sensor wheel may have two GOR optical elements (e.g., ICE cores) with different designs installed on the outer ring and inner ring, respectively, for gas/oil ratio prediction. The first candidate model may include the first optical element channel response as input to make the prediction. The second candidate model may use the second optical element channel input, and a third candidate model may employ both. To characterize each fluid property, the candidate predictive models are calibrated with neural networks using a systematic stepwise input selection algorithm, and saved in a sensor model base for validation analysis at different levels.

FIGS. 7A-7D are plots that show relative prediction variations of candidate models on methane (FIG. 7A), aromatics (FIG. 7B), saturates concentrations (FIG. 7C), and gas/oil ratio (FIG. 7D) with different numbers of channel inputs from the same optical sensor. The relative prediction variation is the root of mean-squared (RMS) error between model predictions and true targets divided by the dynamic range of each particular fluid property in an oil library. As illustrated, there are three curves in each plot. The first curve 702 represents the standard error of calibration (SEC) evaluated on entire fluid samples in an optical-PVT database using synthetic sensor responses. The predictions may be processed with candidate fluid characterization models only. The second curve 704 represents the actual optical sensor responses obtained during manufacturing calibration on the reference fluids listed in the data tables of FIGS. 5A and 5B. The optical inputs are processed with instrument standardization model first before being used as inputs of various fluid predictive models. The third curve 706 is calculated from the tool validation responses using the same reference fluids for manufacturing calibration through pre-calibrated instrument standardization algorithms and fluid characterization algorithms.

It should be noted that the first and second curves 702, 704 comprise calibration curves in developing fluid characterization and instrument standardization models. The SEC for PVT calibration and for optical sensor calibration is usually small when evaluated on the training data. The third curve 706 may prove advantageous in diagnostic analysis since it depicts the impact of questionable optical channel inputs on the ultimate prediction variation through a series of non-linear or linear transfer functions. Although channels Ch03, Ch04, and Ch06 may be questionable by comparing relative output signal difference, as at 606, there are a number of candidate models in each plot from FIGS. 7A-7D with percentage SEC tested on the tool that are smaller than 10%. For this example, the validated candidate models in the existing optical sensor model base are capable of compensating all uncertainties induced through the tool system and generating an acceptable prediction. As will be appreciated, these candidate models can be further tested when the field data with verified fluid properties become available.

Referring again to the method 600 of FIG. 6, if the optical sensor anomaly can be solved by switching to an alternative candidate model, then the optical sensor need not be recalibrated. In other words, the method 600 may further include selecting an alternative candidate model upon detecting an optical sensor anomaly, as at 610. If, however, tool validation variation with existing instrument standardization algorithms and fluid characterization algorithms cannot meet expectations, one or more remedial options may be pursued. Accordingly, the method may optionally include pursuing one or more remedial options when the alternative candidate model fails to correct the optical sensor anomaly, as at 612.

The remedial options may include various options that do not require optical component replacement in the optical sensor. One suitable option that does not require optical component replacement includes rebuilding the fluid predictive models using less affected optical channels as inputs. This can be done by removing the anomalous optical channels and then reconstructing the candidate model base using the remaining available optical channels through either backward stepwise input selection or forward stepwise input selection, while keeping the instrument standardization models unchanged. Another suitable option that does not require optical component replacement includes rebuilding the instrument standardization models. In this approach, the inputs of the instrument standardization model can be the entire tool response data from the tool validation testing or optical sensor calibration data with the questionable optical channels removed, while the fluid predictive models remain unchanged. Yet another suitable option includes developing a new model to compensate the signal difference between optical sensor manufacturing calibration and tool validation by generating a linear or non-linear mapping function on the particular optical channels where the relative difference between the tool validation testing data and the optical sensor validation data is large. In this approach, both sensor-based instrument standardization models and fluid predictive models may remain unchanged.

The remedial options of 612 may further include various options that require optical component replacement in the optical sensor. One suitable option requiring optical component replacement includes substituting anomalous optical elements with new optical elements for the particular sensor wheel. Optical sensor responses may then be collected on the reference fluids through tool validation testing following assembly of the tool. In such a remedial option, only the instrument standardization model associated with particular optical elements or the optical sensor needs to be updated. Another suitable option requiring optical component replacement includes removing the performance degraded sensor wheel from the tool, and replacing it with a newly calibrated sensor wheel (including the associated light source and components). Tool validation testing may then follow. In such a remedial option, only the instrument standardization model and the fluid predictive models associated with the particular optical sensor need to be updated.

Figure 8:
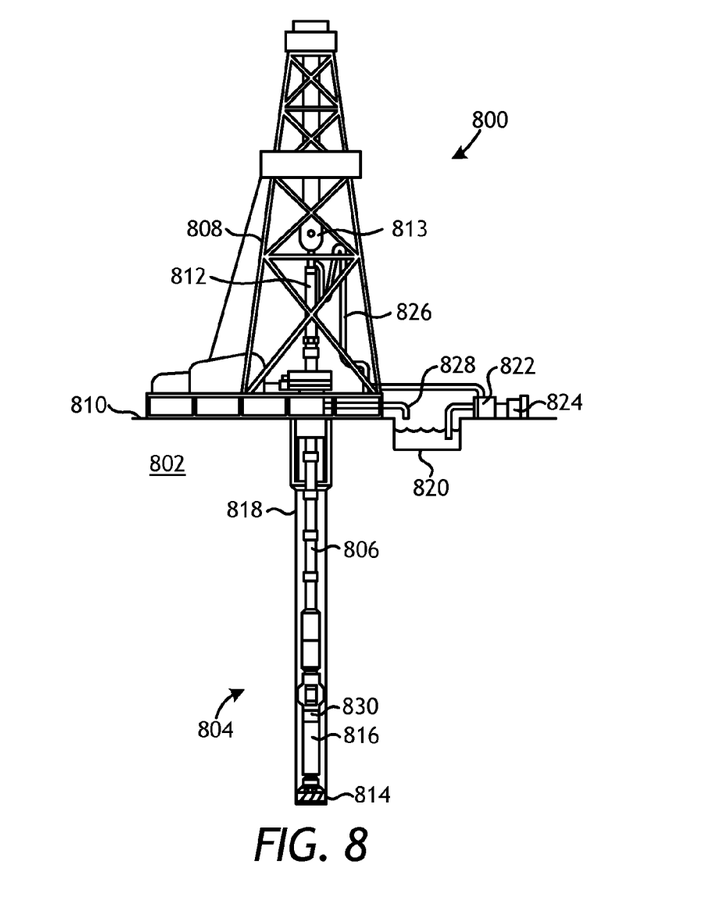
FIG. 8 is a drilling system.

Referring to FIG. 8, illustrated is an exemplary drilling system 800 that may employ one or more principles of the present disclosure. Boreholes may be created by drilling into the earth 802 using the drilling system 800. The drilling system 800 may be configured to drive a bottom hole assembly (BHA) 804 positioned or otherwise arranged at the bottom of a drill string 806 extended into the earth 802 from a derrick 808 arranged at the surface 810. The derrick 808 includes a kelly 812 and a traveling block 813 used to lower and raise the kelly 812 and the drill string 806.

The BHA 804 may include a drill bit 814 operatively coupled to a tool string 816 which may be moved axially within a drilled wellbore 818 as attached to the drill string 806. During operation, the drill bit 814 penetrates the earth 802 and thereby creates the wellbore 818. The BHA 804 provides directional control of the drill bit 814 as it advances into the earth 802. The tool string 816 can be semi-permanently mounted with various measurement tools (not shown) such as, but not limited to, measurement-while-drilling (MWD) and logging-while-drilling (LWD) tools, that may be configured to take downhole measurements of drilling conditions. In other embodiments, the measurement tools may be self-contained within the tool string 816, as shown in FIG. 1.

Fluid or "mud" from a mud tank 820 may be pumped downhole using a mud pump 822 powered by an adjacent power source, such as a prime mover or motor 824. The mud may be pumped from the mud tank 820, through a stand pipe 826, which feeds the mud into the drill string 806 and conveys the same to the drill bit 814. The mud exits one or more nozzles arranged in the drill bit 814 and in the process cools the drill bit 814. After exiting the drill bit 814, the mud circulates back to the surface 810 via the annulus defined between the wellbore 818 and the drill string 806, and in the process returns drill cuttings and debris to the surface. The cuttings and mud mixture are passed through a flow line 828 and are processed such that a cleaned mud is returned down hole through the stand pipe 826 once again.

The BHA 804 may further include a downhole tool or "tool" 830 that may be similar to the downhole tools described herein. More particularly, the tool 830 may have a calibrated optical sensor arranged therein, and the tool 830 may have been calibrated prior to being introduced into the wellbore 818 using the tool validation testing generally described herein. Moreover, prior to being introduced into the wellbore 818, the tool 830 may have been optimized by following the method 600 of FIG. 6.

Figure 9:
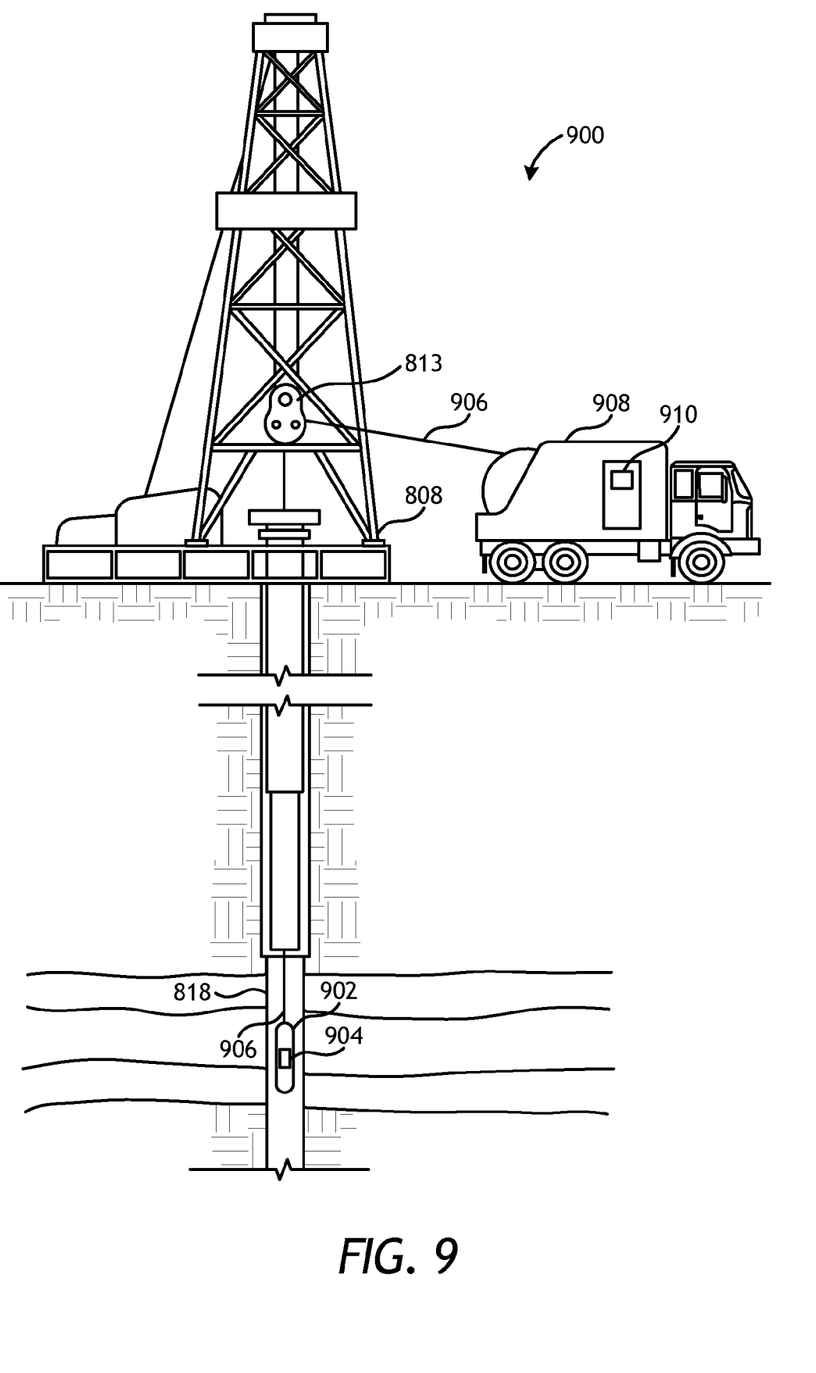
FIG. 9 is a wireline system.

Referring to FIG. 9, illustrated is a wireline system 900 that may employ one or more principles of the present disclosure. During drilling of the wellbore 818, it may be desirable to know the types of formation fluids encountered. The system 900 may include a downhole tool or "tool" 902 that forms part of a wireline logging operation that can include one or more optical sensors 904, as described herein, as part of a downhole measurement tool. The system 900 may include the derrick 808 that supports the traveling block 813. The wireline logging tool 902, such as a probe or sonde, may be lowered by wireline or logging cable 874 into the borehole 812. The tool 902 may be lowered to the bottom of the region of interest and subsequently pulled upward at a substantially constant speed. The tool 902 may be configured to measure fluid properties of the wellbore fluids, and any measurement data generated by the tool 902 and its associated optical sensors 904 can be communicated to a surface logging facility 908 for storage, processing, and/or analysis. The logging facility 908 may be provided with electronic equipment 910, including processors for various types of signal processing.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A method, comprising:
    performing validation testing on a tool having a calibrated optical sensor that includes one or more optical elements, wherein performing the validation testing comprises:
        circulating a plurality of reference fluids through the tool at one or more calibration set points used to calibrate the calibrated optical sensor during an optical sensor calibration; and
        collecting optical sensor responses from an optical channel of each optical element at the one or more calibration set points and thereby obtaining one or more tool sensor responses;

obtaining and pre-processing the one or more tool sensor responses;

comparing the one or more tool sensor responses with calibrated optical sensor responses derived from the calibrated optical sensor during the optical sensor calibration, and detecting one or more optical sensor anomalies in response to a difference between the one or more tool sensor responses and the calibrated optical sensor responses;

evaluating the one or more optical sensor anomalies through performance analysis with one or more candidate models; and selecting an alternative candidate model to mitigate the one or more optical sensor anomalies.

2. The method of claim 1, wherein the one or more calibration set points comprise a same or reduced number of specific temperature and pressure set used to calibrate the calibrated optical sensor.

3. The method of claim 1, wherein obtaining and pre-processing one or more tool responses from the calibrated optical sensor comprises:

directing light to interact with the plurality of reference fluids to produce interacted light;

transmitting the interacted light as energy toward the one or more optical elements of the calibrated optical sensor;

generating detector responses over the one or more optical elements as the one or more tool sensor responses, wherein the one or more tool sensor responses are baseline corrected and normalized to provide normalized tool sensor responses; and converting the normalized tool sensor responses from a tool data space to a calibration data space.

4. The method of claim 1 wherein comparing the one or more tool sensor responses with calibrated optical sensor responses comprises:

calculating a normalized signal response from an optical channel of each optical element during the optical sensor calibration of the calibrated optical sensor to obtain normalized optical sensor signal responses;

calculating a normalized signal response from an optical channel of each optical element during validation testing of the tool to obtain normalized tool sensor responses;

averaging the normalized optical sensor signal responses under one or more temperature and pressure calibration set points;

averaging the normalized tool sensor responses under the one or more temperature and pressure calibration set points; and computing a percentage difference between the normalized optical sensor signal responses and the normalized tool sensor responses with respect to a full dynamic range of optical sensor calibration data on each channel.

5. The method of claim 1, wherein evaluating the one or more optical sensor anomalies through performance analysis with candidate models comprises:

calculating a normalized signal response from an optical channel of each optical element during validation testing of the tool to obtain normalized tool sensor responses;

providing the normalized tool sensor responses into at least one instrument standardization model;

using the at least one instrument standardization model transformed tool sensor responses as candidate inputs of pre-calibrated fluid characterization models;

predicting fluid properties of the plurality of reference fluids with a different number of inputs; and determining if one or more remedial options are needed to mitigate the one or more optical sensor anomalies.

6. The method of claim 5, wherein determining if the one or more remedial options are needed comprises comparing relative prediction variation of tool testing with a variation of optical sensor calibration and optical pressure-volume-temperature (PVT) calibration for each fluid property using the different number of inputs.

7. The method of claim 1, further comprising pursuing one or more remedial options when the alternative candidate model fails to mitigate the one or more optical sensor anomalies.

8. The method of claim 7, wherein pursuing the one or more remedial options comprises selecting a remedial option that requires replacement of one or more of the one or more optical elements.

9. The method of claim 8, further comprising:

substituting only anomalous optical elements in the calibrated optical sensor; and performing a new validation testing on the tool using the plurality of reference fluids.

10. The method of claim 8, wherein the one or more optical elements are disposed on one or more sensor wheels arranged within the calibrated optical sensor, the method further comprising substituting at least one of the one or more sensor wheels in the tool.

11. The method of claim 10, wherein substituting the at least one of the one or more sensor wheels comprises:

removing the at least one of the one or more sensor wheel from the tool;

replacing at least one of the one or more sensor wheels with a newly calibrated sensor wheel and an associated light source and components;

performing a new validation testing on the tool using the plurality of reference fluids.

12. The method of claim 7, wherein pursuing the one or more remedial options comprises selecting a remedial option that does not require replacement of one or more of the one or more optical elements.

13. The method of claim 12, further comprising rebuilding the one or more candidate models using less affected optical channels as inputs.

14. The method of claim 13, wherein rebuilding the one or more candidate models using less affected optical channels as inputs comprises:

removing anomalous optical channels; and reconstructing a candidate model base using other available optical channels through at least one of backward stepwise input selection or forward stepwise input selection, while maintaining instrument standardization models unchanged.

15. The method of claim 12, further comprising rebuilding instrument standardization models.

16. The method of claim 15, wherein rebuilding the instrument standardization models comprises using as model inputs at least one of the one or more tool sensor responses and the calibrated optical sensor responses with questionable optical channels removed, while maintaining fluid predictive models unchanged.

17. The method of claim 12, further comprising developing a new candidate model to compensate for a difference between the one or more tool sensor responses and the calibrated optical sensor responses derived from the calibrated optical sensor during optical sensor calibration.

18. The method of claim 17, wherein developing the new candidate model comprises generating a linear or non-linear mapping function on optical channels where relative differences between the one or more tool sensor responses and the calibrated optical sensor responses are large, while maintaining sensor-based instrument standardization models and fluid predictive models unchanged.

19. The method of claim 1, further comprising:
running the tool into a wellbore as part of a drill string; and
drilling a portion of the wellbore with a drill bit coupled to an end of the drill string.

20. The method of claim 1, further comprising:
running the tool into a wellbore as part of a wireline system; and
measuring one or more fluid properties of a wellbore fluid.

21. A method, comprising:
introducing a tool into a wellbore drilled into one or more subterranean formations, the tool having been previously calibrated for operation by:
performing validation testing on the tool using a plurality of reference fluids, the tool having a calibrated optical sensor installed therein that includes one or more optical elements;
obtaining and pre-processing one or more tool sensor responses from the calibrated optical sensor;
comparing the one or more tool sensor responses obtained during the validation testing with calibrated optical sensor responses derived from the calibrated optical sensor during an optical sensor calibration, and detecting one or more optical sensor anomalies in response to a difference therebetween;
evaluating the one or more optical sensor anomalies through performance analysis with one or more candidate models;
selecting an alternative candidate model to mitigate the one or more optical sensor anomalies; and
pursuing one or more remedial options when the alternative candidate model fails to mitigate the one or more optical sensor anomalies; and
obtaining one or more wellbore parameter measurements with the tool within the wellbore.

22. The method of claim 21, wherein introducing the tool into the wellbore comprises introducing the tool into the wellbore on a wireline.

23. The method of claim 21, wherein introducing the tool into the wellbore comprises introducing the tool into the wellbore as part of a drill string.

* * * * *